(12) United States Patent
Kaur et al.

(10) Patent No.: US 9,067,909 B2
(45) Date of Patent: Jun. 30, 2015

(54) PHOTOACID GENERATOR, PHOTORESIST, COATED SUBSTRATE, AND METHOD OF FORMING AN ELECTRONIC DEVICE

(71) Applicant: Rohm and Haas Electronic Materials LLC, Marlborough, MA (US)

(72) Inventors: Irvinder Kaur, Northborough, MA (US); Emad Aqad, Northborough, MA (US); Cong Liu, Shrewsbury, MA (US); Cheng Bai Xu, Southborough, MA (US)

(73) Assignee: ROHM AND HAAS ELECTRONIC MATERIALS LLC, Marlborough, MA (US)

( * ) Notice: Subject to any disclaimer, the term of this patent is extended or adjusted under 35 U.S.C. 154(b) by 22 days.

(21) Appl. No.: 14/012,577

(22) Filed: Aug. 28, 2013

(65) Prior Publication Data

US 2015/0064620 A1 Mar. 5, 2015

(51) Int. Cl.
G03F 7/004 (2006.01)
G03F 7/20 (2006.01)
C07D 319/04 (2006.01)
C07D 317/72 (2006.01)

(52) U.S. Cl.
CPC ............ *C07D 317/72* (2013.01); *G03F 7/0045* (2013.01); *G03F 7/20* (2013.01); *G03F 7/2002* (2013.01); *C07D 319/04* (2013.01)

(58) Field of Classification Search
CPC ......... G03F 7/004; G03F 7/0045; G03F 7/20; C07D 319/04; C07D 319/06; C07D 319/08
USPC .............. 430/270.1, 322, 919, 921, 923, 924, 430/925; 549/429, 356, 369, 372
See application file for complete search history.

(56) References Cited

U.S. PATENT DOCUMENTS

| | | | |
|---|---|---|---|
| 5,128,232 A | 7/1992 | Thackeray et al. | |
| 5,279,921 A * | 1/1994 | Onishi et al. ............... | 430/270.1 |
| 7,301,047 B2 | 11/2007 | Yoshida et al. | |
| 7,304,175 B2 | 12/2007 | Harada et al. | |
| 7,459,260 B2 | 12/2008 | Chandhok et al. | |
| 8,227,624 B2 | 7/2012 | Nakayashiki et al. | |
| 2005/0079441 A1 | 4/2005 | Takahashi | |
| 2007/0224540 A1 | 9/2007 | Kamimura et al. | |
| 2008/0248422 A1 | 10/2008 | Iwai et al. | |
| 2008/0311522 A1 | 12/2008 | Iwai et al. | |
| 2010/0081088 A1 | 4/2010 | Kawaue et al. | |
| 2010/0239978 A1 | 9/2010 | Wada et al. | |
| 2010/0248149 A1 | 9/2010 | Tsuchimura et al. | |
| 2010/0273105 A1 | 10/2010 | Utsumi et al. | |
| 2010/0304294 A1 | 12/2010 | Ichikawa et al. | |
| 2010/0304296 A1 | 12/2010 | Ichikawa et al. | |
| 2010/0316951 A1 | 12/2010 | Ichikawa et al. | |
| 2011/0014568 A1 | 1/2011 | Ichikawa et al. | |
| 2012/0009521 A1 | 1/2012 | Kawaue et al. | |
| 2012/0065291 A1 | 3/2012 | Matsumura et al. | |
| 2012/0135351 A1 | 5/2012 | Ichikawa et al. | |
| 2012/0136155 A1 | 5/2012 | Makabe et al. | |
| 2013/0344438 A1 | 12/2013 | Aqad et al. | |

FOREIGN PATENT DOCUMENTS

| | | |
|---|---|---|
| CN | 102289149 A | 12/2011 |
| EP | 0164248 A2 | 12/1985 |
| EP | 0783136 A2 | 7/1997 |

(Continued)

OTHER PUBLICATIONS

Non-Final Office Action dated Nov. 20, 2014; U.S. Appl. No. 13/925,926, filed Jun. 25, 2013.
U.S. Appl. No. 13/854,078, filed Mar. 30, 2013, "Acid Generators and Photoresists Comprising the Same"; 35 Pages.
U.S. Appl. No. 14/063,148, filed Oct. 25, 2013, "Photoacid Generator, Photoresist, Coated Substrate, and Method of Forming an Electronic Device"; 34 Pages.
U.S. Appl. No. 13/661,553, filed Oct. 26, 2012, "Photoacid Generating Compound and Photoresist Composition Comprising Same, Coated Article Comprising the Photoresist and Method of Making an Article"; 30 Pages.
Non-Final Office Action dated Jan. 13, 2015; U.S. Appl. No. 14/063,148, filed Oct. 25, 2013.
Xie et al. "Isolation, Structure Identification and SAR Studies on Thiosugar Sulfonium Salts, Neosalaprinol and Neoponkoranol, as potent α-glucosidase inhibitors" Bioorganic & Medicinal Chemistry 19 (2011) 2015-2022.

*Primary Examiner* — Anca Eoff
(74) *Attorney, Agent, or Firm* — Cantor Colburn LLP

(57) ABSTRACT

A photoacid generator compound has formula (1)

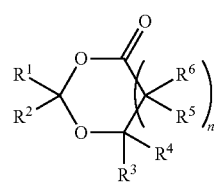

wherein n is zero or 1; and $R^1$-$R^6$ are each independently hydrogen, halogen, or unsubstituted or substituted $C_{1-20}$ linear or branched alkyl, $C_{1-20}$ cycloalkyl, $C_{6-20}$ aryl, $C_{3-20}$ heteroaryl, or an acid-generating group having the structure

*-[-L-Z⁻M⁺]

wherein L is an unsubstituted or substituted $C_{1-50}$ divalent group; $Z^-$ is a monovalent anionic group; and $M^+$ is an iodonium or sulfonium cation. Geminal R groups can combine to form a ring with the carbon to which they are attached, as long as no more than two such rings are formed. At least one of $R^1$-$R^6$ includes the acid-generating group or two germinal R groups combine to form the acid-generating group. Also described are a photoresist composition incorporating the photoacid generator compound, a coated substrate including a layer of the photoresist composition, and a method of forming an electronic device using a layer of the photoresist composition.

19 Claims, No Drawings

(56) References Cited

FOREIGN PATENT DOCUMENTS

| EP | 0829766 | A2 | 3/1998 |
| EP | 1906241 | A1 | 4/2008 |
| JP | 2011201860 | A | 10/2011 |
| JP | 2011201866 | A | 10/2011 |
| JP | 2011256390 | A | 12/2011 |
| JP | 2014-105166 | * | 6/2014 |
| WO | WO 2011/162408 | * | 12/2011 |

* cited by examiner

PHOTOACID GENERATOR, PHOTORESIST, COATED SUBSTRATE, AND METHOD OF FORMING AN ELECTRONIC DEVICE

FIELD

The present invention relates to photoacid generators and their use in photoresist compositions.

INTRODUCTION

Advanced lithographic techniques such as 193 nanometer immersion lithography have been developed to achieve high quality and smaller feature sizes in microlithography processes, for purposes of forming ever-smaller logic and memory transistors. It is important to achieve both smaller critical dimension (CD) in the imaged photoresist used in the microlithography process, and for the photoresists to provide both the lowest line edge roughness (LER) and line width roughness (LWR), while still retaining good process control tolerances such as high exposure latitude (EL) and a wide depth of focus (DOF). Also important is low mask error factor (MEF), which is defined as the ratio of critical dimension (CD) change on the resolved resist pattern to the dimension change on the mask pattern.

To meet the challenges for photoresist materials raised by high resolution lithography, photoacid generators (PAGs) have been made that are soluble in aqueous developers and have low absorbance. A variety of photoacid generators (PAGs) used for formulating photoresists are known. However, a need remains for PAGs that provide photoresist compositions with one or more of increased exposure latitude, decreased mask error factor, and decreased line width roughness.

SUMMARY

One embodiment is a photoacid generator compound having the formula (1)

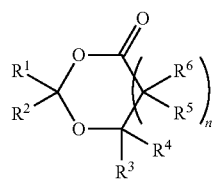

wherein n is zero or 1; and $R^1$, $R^2$, $R^3$, $R^4$, $R^5$, and $R^6$ are each independently hydrogen, halogen, unsubstituted or substituted $C_{1-20}$ linear or branched alkyl, unsubstituted or substituted $C_{1-20}$ cycloalkyl, unsubstituted or substituted $C_{6-20}$ aryl, unsubstituted or substituted $C_{3-20}$ heteroaryl, or a monovalent group having the structure

\*—[-L-Z⁻M⁺]

wherein L is an unsubstituted or substituted $C_{1-50}$ divalent group; $Z^-$ is a monovalent anionic group selected from carboxylate, sulfate, sulfonate, sulfamate, sulfonamidate (anion of sulfonamide), and sulfonimidate (anion of sulfonimide); and $M^+$ is a cation selected from disubstituted iodonium ions and trisubstituted sulfonium ions; wherein $R^1$ and $R^2$ can be taken together to form a ring and/or $R^3$ and $R^4$ can be taken together to form a ring and/or $R^5$ and $R^6$ can be taken together to form a ring, provided that no more than two rings are collectively formed by $R^1$, $R^2$, $R^3$, $R^4$, $R^5$, and $R^6$, and provided that one of $R^1$, $R^2$, $R^3$, $R^4$, $R^5$, and $R^6$ has the structure

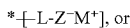

$R^1$ and $R^2$ are taken together to form

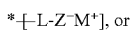

$R^3$ and $R^4$ are taken together to form

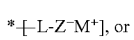

$R^5$ and $R^6$ are taken together to form

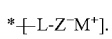

Another embodiment is a photoresist composition comprising an acid-sensitive polymer, and the photoacid generator compound above.

Another embodiment is a coated substrate comprising: (a) a substrate having one or more layers to be patterned on a surface thereof; and (b) a layer of the photoresist composition over the one or more layers to be patterned.

Another embodiment is a method of forming an electronic device, comprising: (a) applying a layer of the photoresist composition on a substrate; (b) pattern-wise exposing the photoresist composition layer to activating radiation; and (c) developing the exposed photoresist composition layer to provide a resist relief image.

These and other embodiments are described in detail below.

DETAILED DESCRIPTION

The present inventors have determined that a particular type of photoacid generating compound provides photoresist compositions with one or more of increased exposure latitude, decreased mask error factor, and decreased line width roughness. Specifically, the photoacid generating compound contains an acid-labile 1,3-dioxolan-4-one or 1,3-dioxan-4-one moiety. While not wishing to be bound by any particular mechanism of operation, the present inventors believe that the acetal or ketal functionality of the 1,3-dioxolan-4-one or 1,3-dioxan-4-one moiety reacts with acid generated during the post-exposure bake (PEB), generating a compound with a hydroxyl group and a carboxylic acid group acid that ionizes in the subsequent basic developer step (see Scheme 1).

Scheme 1

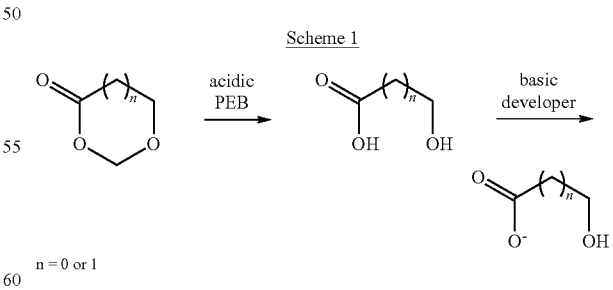

n = 0 or 1

Thus, the photoacid generating compound provides limited diffusion during the post-exposure bake step, and enhanced diffusion during the development step.

Thus, one embodiment is a photoacid generator compound having the formula (I)

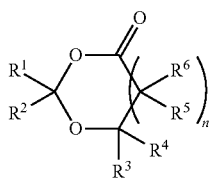
(I)

wherein n is zero or 1; and $R^1$, $R^2$, $R^3$, $R^4$, $R^5$, and $R^6$ are each independently hydrogen, halogen, unsubstituted or substituted $C_{1-20}$ linear or branched alkyl, unsubstituted or substituted $C_{1-20}$ cycloalkyl, unsubstituted or substituted $C_{6-20}$ aryl, unsubstituted or substituted $C_{3-20}$ heteroaryl, or a monovalent group having the structure

*—[-L-$Z^-$$M^+$]

wherein L is an unsubstituted or substituted $C_{1-50}$ divalent group; $Z^-$ is a monovalent anionic group selected from carboxylate, sulfate, sulfonate, sulfamate, sulfonamidate (anion of sulfonamide), and sulfonimidate (anion of sulfonimide); and $M^+$ is a cation selected from disubstituted iodonium ions and trisubstituted sulfonium ions; wherein $R^1$ and $R^2$ can be taken together to form a ring and/or $R^3$ and $R^4$ can be taken together to form a ring and/or $R^5$ and $R^6$ can be taken together to form a ring, provided that no more than two rings are collectively formed by $R^1$, $R^2$, $R^3$, $R^4$, $R^5$, and $R^6$, and provided that one of $R^1$, $R^2$, $R^3$, $R^4$, $R^5$, and $R^6$ has the structure

*—[-L-$Z^-$$M^+$], or $R^1$ and $R^2$ are taken together to form

*—[-L-$Z^-$$M^+$], or $R^3$ and $R^4$ are taken together to form

*—[-L-$Z^-$$M^+$], or $R^5$ and $R^6$ are taken together to form

*—[-L-$Z^-$$M^+$].

As used herein, "substituted" means including at least one substituent such as a halogen (i.e., F, Cl, Br, I), hydroxyl, amino, thiol, carboxyl, carboxylate, amide, nitrile, sulfide, disulfide, nitro, $C_{1-18}$ alkyl, $C_{1-18}$ alkoxyl, $C_{2-18}$ alkenyl, $C_{2-18}$ alkenoxyl, $C_{6-18}$ aryl, $C_{6-18}$ aryloxyl, $C_{7-18}$ alkylaryl, or $C_{7-18}$ alkylaryloxyl. It will be understood that any group or structure disclosed with respect to the formulas herein can be so substituted unless otherwise specified. Also, "fluorinated" means having one or more fluorine atoms incorporated into the group. For example, where a $C_{1-18}$ fluoroalkyl group is indicated, the fluoroalkyl group can include one or more fluorine atoms, for example, a single fluorine atom, two fluorine atoms (e.g., as a 1,1-difluoroethyl group), three fluorine atoms (e.g., as a 2,2,2-trifluoroethyl group), or fluorine atoms at each free valence of carbon (e.g., as a perfluorinated group such as —$CF_3$, —$C_2F_5$, —$C_3F_7$, or —$C_4F_9$).

In some embodiments of the formula (1) PAG, n is 0, in which case the PAG is a substituted 1,3-dioxolane-4-one. In other embodiments of the formula (1) PAG, n is 1, in which case the PAG is a substituted 1,3-dioxane-4-one.

In formula (1), $R^1$, $R^2$, $R^3$, $R^4$, $R^5$, and $R^6$ are each independently hydrogen, halogen, unsubstituted or substituted $C_{1-20}$ linear or branched alkyl, unsubstituted or substituted $C_{1-20}$ cycloalkyl, unsubstituted or substituted $C_{6-20}$ aryl, unsubstituted or substituted $C_{3-20}$ heteroaryl, or a monovalent group having the structure

*—[-L-$Z^-$$M^+$]

wherein L is an unsubstituted or substituted $C_{1-50}$ divalent group; $Z^-$ is a monovalent anionic group selected from carboxylate, sulfate, sulfonate, sulfamate, sulfonamidate (anion of sulfonamide), and sulfonimidate (anion of sulfonimide); and $M^+$ is a cation selected from disubstituted iodonium ions and trisubstituted sulfonium ions. Examples of unsubstituted or substituted $C_{1-20}$ linear or branched alkyl groups include methyl, ethyl, n-propyl, i-propyl, n-butyl, i-butyl, t-butyl, diphenylmethyl, 2-phenylpropan-2-yl, 1,1-diphenylethan-1-yl, and triphenylmethyl. Examples of unsubstituted or substituted $C_{3-20}$ cycloalkyl groups include cyclopentyl, cyclohexyl, methylcyclohexan-1-yl, ethylcyclohexan-1-yl, 1-norbornyl, 2-norbornyl, 7-norbornyl, 1-adamantlyl, 2-adamantlyl, 2-methylbicyclo[2.2.1]heptan-2-yl, and 2-methyladamantan-2-yl. Examples of unsubstituted or substituted $C_{6-20}$ aryl include phenyl, 1-naphthyl, and 2-naphthyl. Examples of unsubstituted or substituted $C_{3-20}$ heteroaryl include 2-imidazolyl, 4-imidazolyl, 2-pyridyl, 3-pyridyl, and 4-pyridyl.

In formula (1), $R^1$ and $R^2$ can be taken together to form a ring and/or $R^3$ and $R^4$ can be taken together to form a ring and/or $R^5$ and $R^6$ can be taken together to form a ring, provided that no more than two rings are collectively formed by $R^1$, $R^2$, $R^3$, $R^4$, $R^5$, and $R^6$. In these embodiments, it will be understood that the ring includes the carbon atom to which $R^1$ and $R^2$ are bound. Examples of $R^1$ and $R^2$ forming a ring include

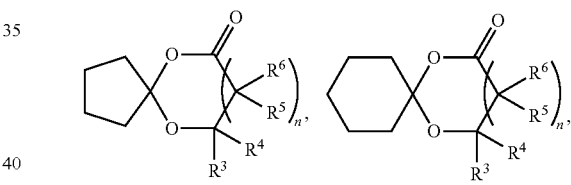

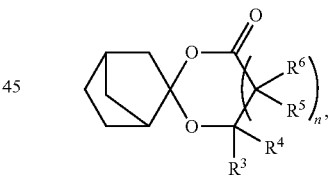

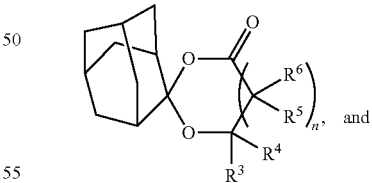

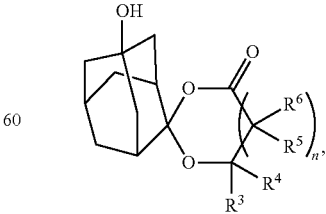

wherein n is zero or 1. Examples of $R^3$ and $R^4$ forming a ring include

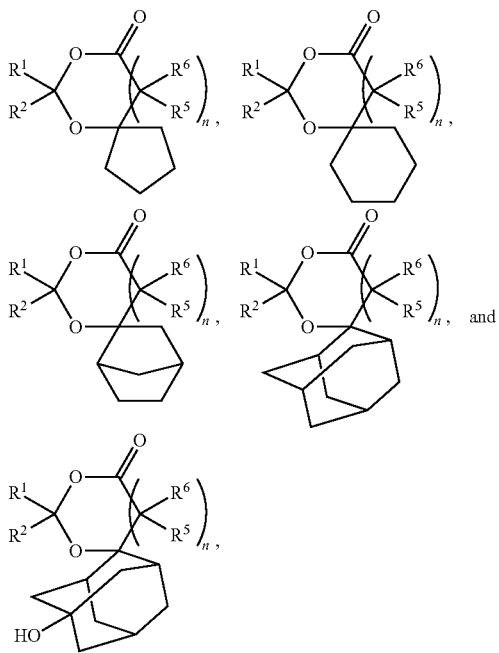

wherein n is zero or 1. Examples of $R^5$ and $R^6$ forming a ring include

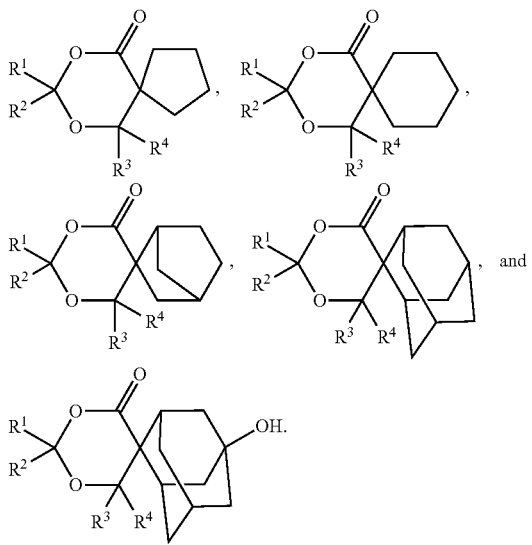

In formula (1), L is an unsubstituted or substituted $C_{1-50}$ divalent group. Examples of unsubstituted or substituted $C_{1-50}$ divalent groups include unsubstituted or substituted $C_{1-20}$ linear or branched alkylene (e.g., methane-1,1-diyl (—CH$_2$—), ethane-1,2-diyl (—CH$_2$CH$_2$—), ethane-1,1-diyl (—CH(CH$_3$)—), propane-2,2-diyl (—C(CH$_3$)$_2$—)), unsubstituted or substituted $C_{3-20}$ cycloalkylene (e.g., 1,1-cyclopentanediyl, 1,2-cyclopentanediyl, 1,1-cyclohexanediyl, 1,4-cyclohexanediyl, norbornanediyl, and adamantanediyl), unsubstituted or substituted $C_{6-20}$ arylene (e.g., 1,3-phenylene, 1,4-phenylene, 1,4-naphthylene, 1,5-naphthylene, and 2,6-naphthylene), and unsubstituted or substituted $C_{3-20}$ heteroarylene (e.g., imidazo-2,4-ylene, 2,4-pyridylene, and 2,5-pyridylene).

In formula (1), $Z^-$ is a monovalent anionic group selected from carboxylate, sulfate, sulfonate, sulfamate, sulfonamidate (anion of sulfonamide), and sulfonimidate (anion of sulfonimide). In some embodiments, $Z^-$ is a sulfonate.

In formula (1), M is a cation selected from disubstituted iodonium ions and trisubstituted sulfonium ions. Disubstituted iodonium ions can have the structure

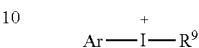

wherein Ar is substituted or unsubstituted $C_{6-30}$ aryl, or unsubstituted or substituted $C_{3-20}$ heteroaryl; and $R^9$ is unsubstituted or substituted $C_{1-20}$ linear or branched alkyl, unsubstituted or substituted $C_{1-20}$ cycloalkyl, unsubstituted or substituted $C_{6-20}$ aryl, or unsubstituted or substituted $C_{3-20}$ heteroaryl. Ar and $R^9$ can, optionally, be bonded to each other to form a ring with the iodine atom. Trisubstituted sulfonium ions can have the structure

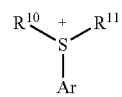

wherein Ar is substituted or unsubstituted $C_{6-30}$ aryl, or unsubstituted or substituted $C_{3-20}$ hetero aryl; and $R^{10}$ and $R^{11}$ are each independently unsubstituted or substituted $C_{1-20}$ linear or branched alkyl, unsubstituted or substituted $C_{1-20}$ cycloalkyl, unsubstituted or substituted $C_{6-20}$ aryl, or unsubstituted or substituted $C_{3-20}$ heteroaryl. In some embodiments, $R^{10}$ and $R^{11}$ are bonded to each other to form a ring with the sulfur atom. In some embodiments, $R^{10}$ or $R^{11}$ is bonded to Ar to form a ring with the sulfur atom.

In some embodiments, $M^+$ is a trisubstituted sulfonium ion having formula (4), (5), (6), (7)

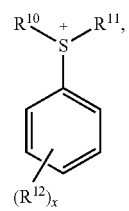

(4)

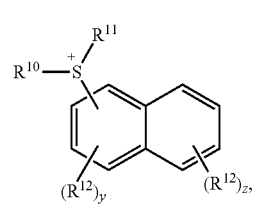

(5)

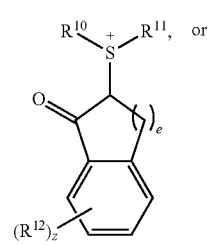

(6)

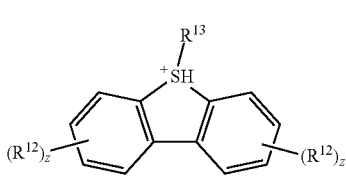  (7)

wherein each occurrence of $R^{10}$, $R^{11}$, and $R^{12}$ is independently unsubstituted or substituted $C_{1-20}$ linear or branched alkyl, unsubstituted or substituted $C_{1-20}$ cycloalkyl, unsubstituted or substituted $C_{6-20}$ aryl, or unsubstituted or substituted $C_{3-20}$ heteroaryl, and $R^{10}$ and $R^{11}$ are optionally bonded to each other to form a ring with the sulfur atom; e is 0 to 4, x is 0 to 5, y is 0 to 3, and each occurrence of z is independently 0 to 4. In some embodiments, $M^+$ is a triphenylsulfonium ion, or a phenyl dibenzothiophenium ion.

In some embodiments, the photoacid generator compound has the formula (2a)

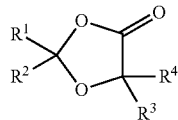  (2a)

wherein $R^3$ or $R^4$ is

*—[—L—SO$_3^-$M$^+$], or $R^3$ and $R^4$ are taken together to form

*—[—L—SO$_3^-$M$^+$]; and $R^1$, $R^2$, L, and $M^+$ are as defined above. In some embodiments, $R^1$ and $R^2$ are taken together to form a ring. For example, $R^1$ and $R^2$ and the carbon to which they are bonded can form an adamantyl ring, so that the photoacid generator compound has the structure

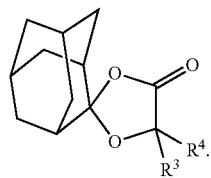

In some embodiments in which the photoacid generator compound has the formula (2a), L is a substituted $C_{1-50}$ divalent group, $L^1$, having the formula (3)

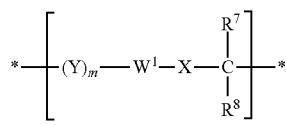  (3)

wherein m is zero or 1, Y is an unsubstituted or substituted $C_{1-20}$ alkylene, $W^1$ is an unsubstituted or substituted divalent $C_{5-20}$ alicyclic group, X is an unsubstituted or substituted $C_{1-20}$ alkylene, and $R^7$ and $R^8$ are each independently fluorine, or partially fluorinated $C_{1-12}$ alkyl, or perfluorinated $C_{1-12}$ alkyl.

In the context of the limitation, "Y is an unsubstituted or substituted $C_{1-20}$ alkylene", it will be understood that substituted $C_{1-20}$ alkylene includes not only species with one or more monovalent substituents appended to the alkylene group, but also divalent substituents within the main chain of the alkylene group. For example, substituted $C_{1-20}$ alkylene includes

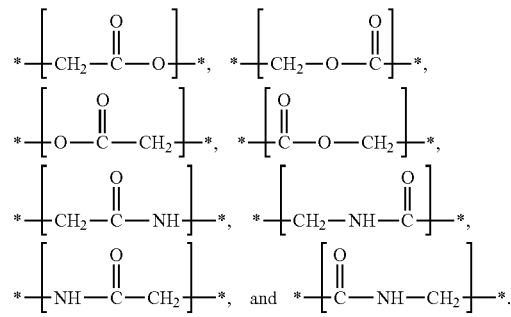

Similarly, in the context of the limitation, "X is an unsubstituted or substituted $C_{1-20}$ alkylene", it will be understood that substituted $C_{1-20}$ alkylene includes not only species with one or more monovalent substituents appended to the alkylene group, but also divalent substituents within the main chain of the alkylene group. For example, substituted $C_{1-20}$ alkylene includes

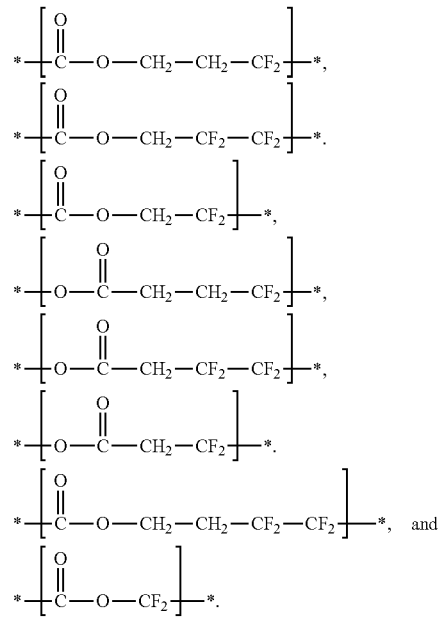

Specific examples of photoacid generator compounds having formula (2a) include

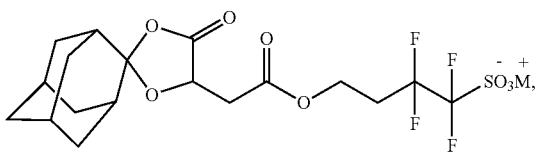

-continued

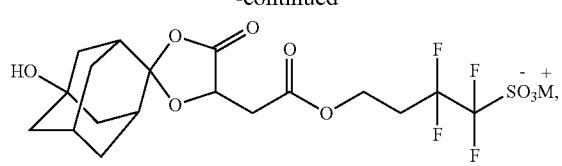
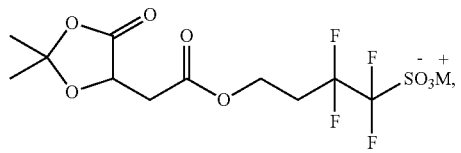
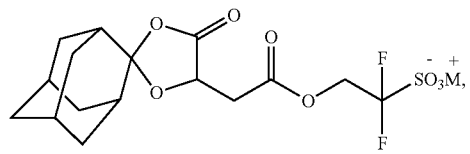
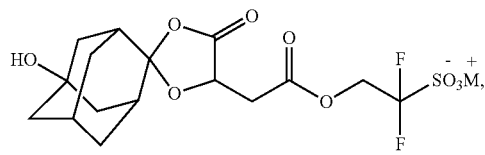
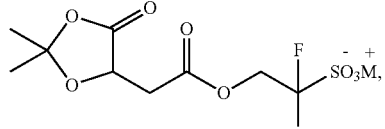
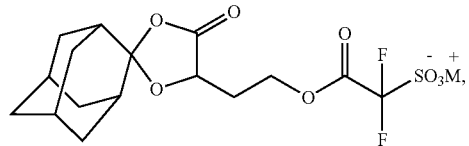
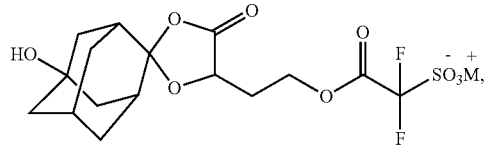
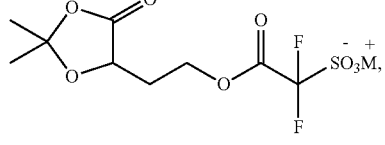
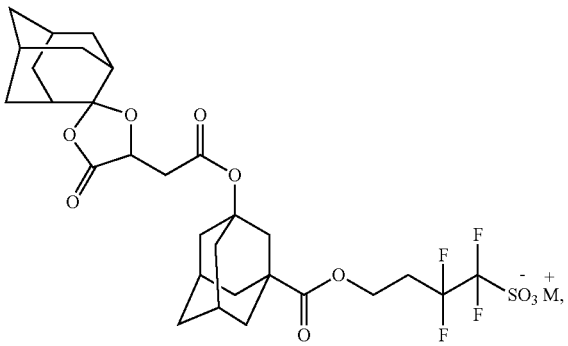

-continued

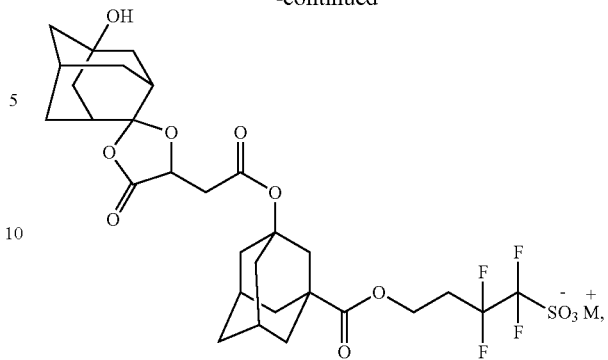
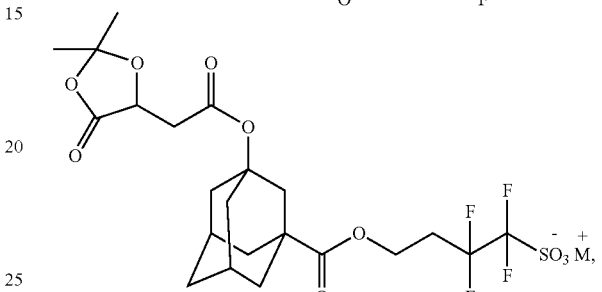
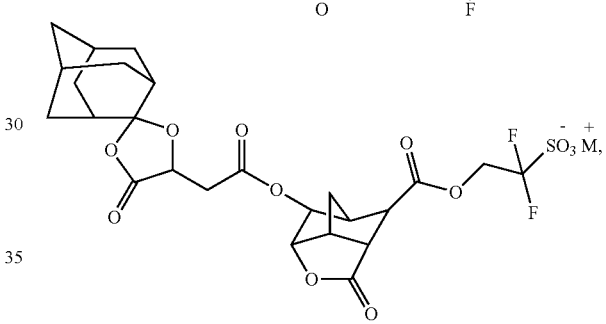

and combinations thereof, wherein $M^+$ is as defined above.

In some embodiments in which the photoacid generator compound has the formula (2a) and L is a substituted $C_{1-50}$ divalent group, $L^1$, having formula (3), $W^1$ is an adamantylene group, such as, for example,

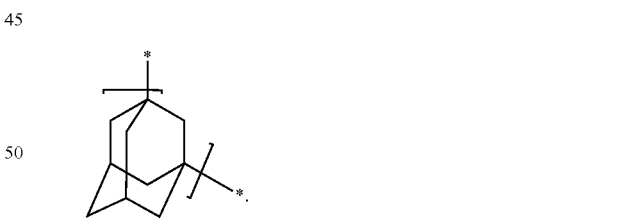

In some embodiments, the photoacid generator compound has the formula (2b)

(2b)

wherein $R^1$ or $R^2$ is $*\text{-}[\text{-}L\text{-}SO_3^-M^+]$, or $R^1$ and $R^2$ are taken together to form

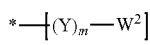
and $R^3$, $R^4$, L, and $M^+$ are as defined above.

In specific embodiments in which the photoacid generator compound has the formula (2b), $R^2$ and $R^3$ are hydrogen; $R^4$ has the structure

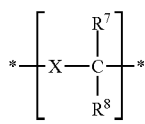

wherein m is zero or 1, Y is an unsubstituted or substituted $C_{1-20}$ alkylene, and $W^2$ is an unsubstituted or substituted monovalent $C_{5-20}$ alicyclic group; and L is a substituted $C_{1-50}$ divalent group, $L^2$, having the structure

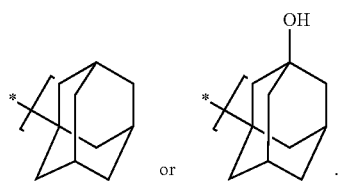

wherein X is an unsubstituted or substituted $C_{1-20}$ alkylene, and $R^7$ and $R^8$ are each independently fluorine, or partially fluorinated $C_{1-12}$ alkyl, or perfluorinated $C_{1-12}$ alkyl. In a subset of these specific embodiments, $W^2$ is an unsubstituted or substituted adamantyl group, such as, for example,

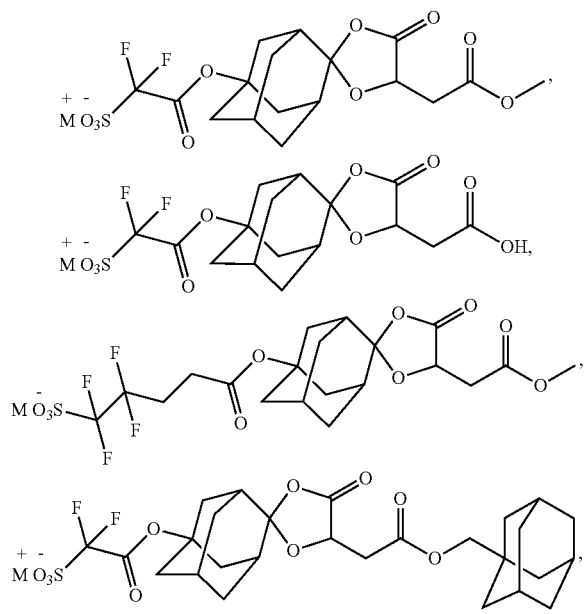

Specific examples of photoacid generator compound having the formula (2b) include

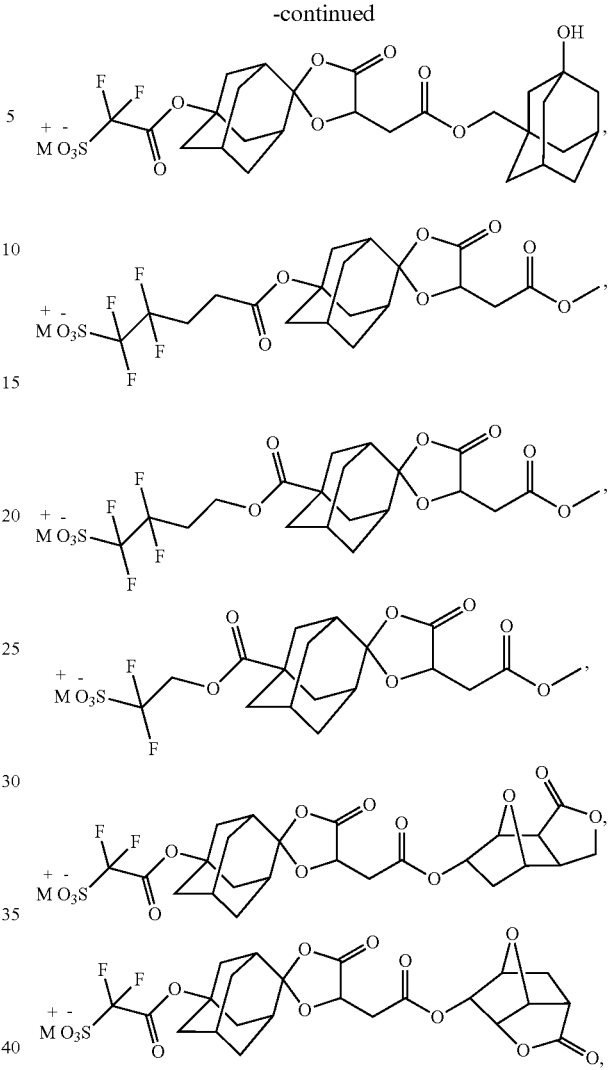

and combinations thereof; wherein $M^+$ is as defined above.

The photoacid generator compound can include a polymerizable double bond to facilitate its incorporation into a copolymer. Functional groups with polymerizable double bonds include (meth)acrylate, vinyl ether, and norbornenyl. Alternatively, or in addition, where the photoacid generator compound includes a vinyl ether group, linking to the copolymer can be through a ketal or acetal linkage. In these embodiments, the functional groups are considered a substituent on the substituted embodiments of $R^1$-$R^6$ of formula (1).

The photoacid generator compound is a useful component of photoresist compositions. Thus, one embodiment is a photoresist composition comprising: an acid-sensitive polymer, and the photoacid generator compound in any of its above-described variations. Acid-sensitive polymers useful for forming a photoresist in combination with the photoacid generator compound include the copolymerization products of monomers comprising acid-deprotectable monomers, base-soluble monomers, dissolution rate modifying monomers, and etch-resistant monomers. Any such monomers or combinations of monomers suitable for forming, for example, a 193 nanometer photoresist polymer can be used. In some embodiments, a combination of monomers is used, which include at least two different monomers selected from a (meth)acrylate monomer having an acid-deprotectable group (deprotection of which yields a base-soluble group), a (meth)acrylate monomer having a lactone functional group, and a (meth)acrylate monomer having a base-soluble group not identical to the acid-deprotectable base soluble group. The acid-sensitive polymer can include at least three different monomers, at least one of which is selected from each of the foregoing monomer types. Other monomers, such as a (meth)acrylate monomer for improving adhesion or etch-resistance, can also be included.

Any acid-deprotectable monomer useful for forming a 193 nanometer photoresist polymer can be used. Exemplary acid-deprotectable monomers include

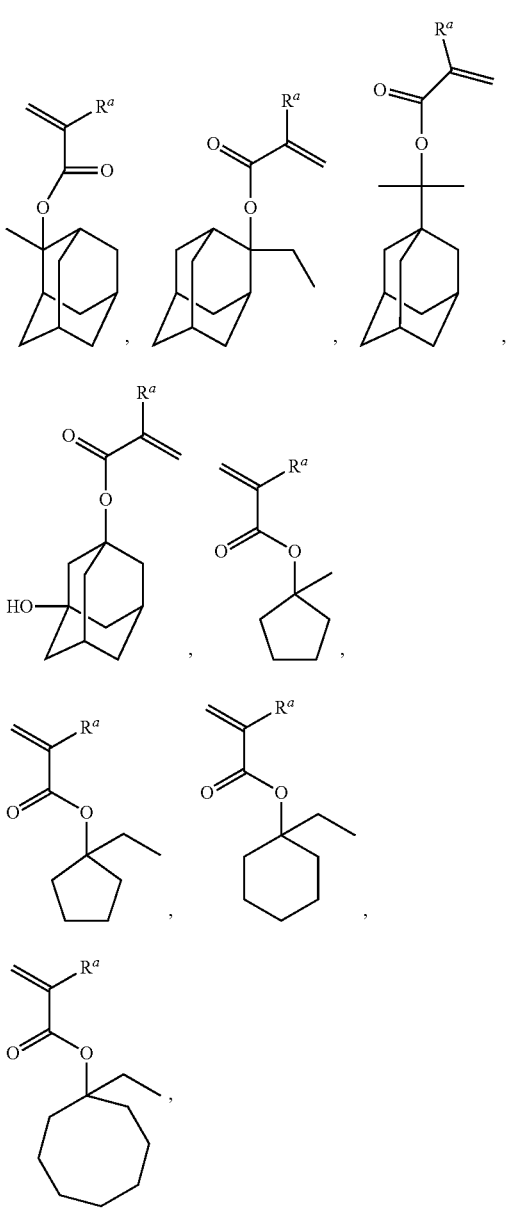

and combinations thereof, wherein $R^a$ is H, F, CN, $C_{1\text{-}10}$ alkyl, or $C_{1\text{-}10}$ fluoroalkyl.

Any lactone-containing monomer useful for forming a 193 nanometer photoresist polymer can be used. Exemplary such lactone-containing monomers include

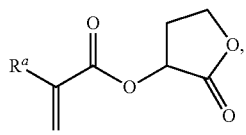

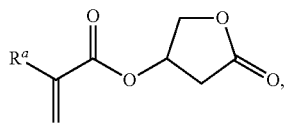

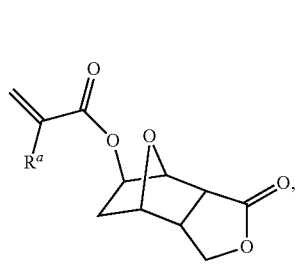

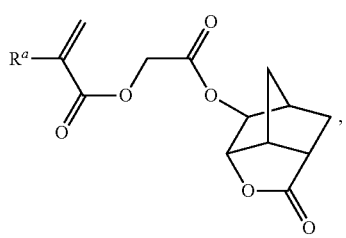

and combinations thereof, wherein $R^a$ is H, F, CN, $C_{1\text{-}10}$ alkyl, or $C_{1\text{-}10}$ fluoroalkyl.

Any base-soluble monomer useful for forming a 193 nanometer photoresist polymer can be used. Exemplary additional base-soluble (meth)acrylate monomers include

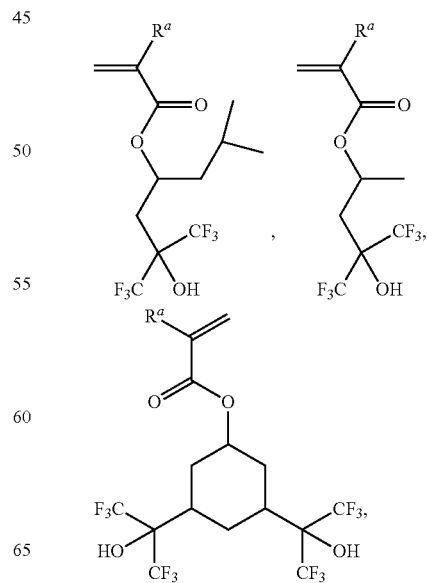

-continued

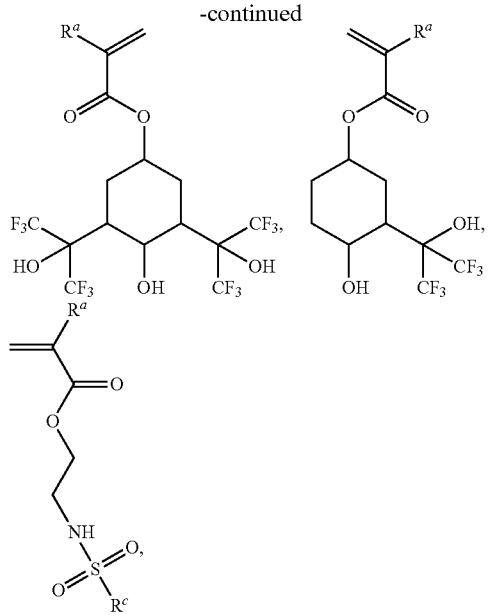

and combinations thereof, wherein $R^a$ is H, F, CN, $C_{1-10}$ alkyl, or $C_{1-10}$ fluoroalkyl, and $R^c$ is a $C_{1-4}$ perfluoroalkyl group.

The photoacid generator compound is combined with the acid-sensitive polymer, either in admixture or by copolymerization, to form a photoresist composition. The photoresist composition optionally further includes a second acid-sensitive polymer, a second photoacid generator compound, an amine or amide additive to adjust photospeed and/or acid diffusion, a solvent, a surfactant, or a combination thereof.

The second acid-sensitive polymer can be any polymer suitable for formulating photoresists for use at 193 nanometers. Such acid-sensitive polymers include an acid sensitive polymer comprising acid sensitive groups and lactone-containing groups, where the acid sensitive group deprotects a base-soluble group on exposure to acid.

The photoresist composition can include an amine or amide compound, referred to herein as a quencher. Quenchers can more broadly include, for example, those based on hydroxides, carboxylates, amines, imines, and amides. In an embodiment, a useful quencher is an amine, an amide, or a combination thereof. Specifically, such quenchers include $C_{1-30}$ organic amines, imines, or amides, or can be a $C_{1-30}$ quaternary ammonium salt of a strong base (e.g., a hydroxide or alkoxide) or a weak base (e.g., a carboxylate). Exemplary quenchers include amines such as Troger's base, a hindered amine such as diazabicycloundecene (DBU) or diazabicyclononene (DBN), N-protected amines such as N-t-butylcarbonyl-1,1-bis(hydroxymethyl)-2-hydroxyethylamine (TBOC-TRIS), or ionic quenchers including quaternary alkyl ammonium salts such as tetrabutylammonium hydroxide (TBAH) or tetrabutyl ammonium lactate.

Solvents generally suitable for dissolving, dispensing, and coating the components include anisole, alcohols including ethyl lactate, methyl 2-hydroxybutyrate (HBM), 1-methoxy-2-propanol (also referred to as propylene glycol methyl ether, PGME), and 1-ethoxy-2 propanol, esters including n-butyl acetate, 1-methoxy-2-propyl acetate (also referred to as propylene glycol methyl ether acetate, PGMEA), methoxyethyl propionate, ethoxyethyl propionate, and gamma-butyrolactone, ketones including cyclohexanone and 2-heptanone, and combinations thereof.

Surfactants include fluorinated and non-fluorinated surfactants, and are preferably non-ionic. Exemplary fluorinated non-ionic surfactants include perfluoro $C_4$ surfactants such as FC-4430 and FC-4432 surfactants, available from 3M Corporation; and fluorodiols such as POLYFOX PF-636, PF-6320, PF-656, and PF-6520 fluorosurfactants from Omnova.

The photoacid generator compound is present in the photoresist in an amount of 0.01 to 20 weight percent, specifically 0.1 to 15 weight percent, based on the total weight of solids in the photoresist composition. Where a polymer-bound photoacid generator is used, the polymer-bound photoacid generator as the corresponding monomer is present in the same amount. The polymer content can be present in an amount of 50 to 99 weight percent, specifically 55 to 95 weight percent, more specifically 60 to 90 weight percent, and still more specifically 65 to 90 based on the total weight of solids in the photoresist composition. It will be understood that "polymer" used in this context of a component in a photoresist can mean only the acid-sensitive polymer described herein, or a combination of the acid-sensitive polymer with another polymer useful in a photoresist. A surfactant can be included in an amount of 0.01 to 5 weight percent, specifically 0.1 to 4 weight percent, and still more specifically 0.2 to 3 weight percent, based on the total weight of solids in the photoresist composition. A quencher can be included in relatively small amounts of for example, from 0.03 to 5 weight percent based on the total weight of solids in the photoresist composition. Other additives such as embedded barrier layer (EBL) materials for immersion lithography applications can be included in amounts of less than or equal to 30 weight percent, specifically less than or equal to 20 weight percent, or more specifically less than or equal to 10 weight percent, based on the total weight of solids weight percent. The total solids content of the photoresist composition can be 0.5 to 50 weight percent, specifically 1 to 45 weight percent, more specifically 2 to 40 weight percent, and still more specifically 5 to 35 weight percent, based on the total weight of solids and solvent. It will be understood that the "solids" includes copolymer, photoacid generator, quencher, surfactant, and any optional additives, exclusive of solvent.

The photoresist disclosed herein can be used to form a film comprising the photoresist, where the film on the substrate constitutes a coated substrate. Such a coated substrate includes: (a) a substrate having one or more layers to be patterned on a surface thereof; and (b) a layer of the photoresist composition over the one or more layers to be patterned. Preferably, patterning is carried out using ultraviolet radiation at wavelength of less than 248 nm, and in particular, at 193 nm. The patternable film thus comprises the photoacid generator compound. A method of forming an electronic device includes: (a) applying a layer of a photoresist composition of claim 7 on a substrate; (b) pattern-wise exposing the photoresist composition layer to activating radiation; and (c) developing the exposed photoresist composition layer to provide a resist relief image. In some embodiments, the radiation is extreme ultraviolet (EUV) or electron beam (e-beam) radiation.

Developing the pattern can be accomplished by either positive tone development (PTD) in which the pattern-wise exposed region is removed by the action of an aqueous base developer such as aqueous tetramethylammonium hydroxide (TMAH). An exemplary positive tone developer is 0.26 Normal aqueous TMAH. Alternatively, the same pattern-wise exposure can be developed using an organic solvent developer to provide a negative tone development (NTD) in which the unexposed region of a pattern is removed by the action of a negative tone developer. Useful solvents for negative tone development include those also useful for dissolving, dispensing, and coating. Exemplary negative tone developer solvents include propylene glycol methyl ether acetate (PGMEA), methyl 2-hydroxyisobutyrate (HBM), methoxyethyl propionate, ethoxyethyl propionate, and gamma-butyrolactone, cyclohexanone, 2-heptanone, and combinations thereof. A method of making a pattern thus includes patternwise exposing a photoresist composition layer with actinic radiation, and developing the pattern by treatment with an aqueous alkaline developer to form a positive tone relief image, or with an organic solvent developer to form a negative tone relief image.

Substrates can be any dimension and shape, and are preferably those useful for photolithography, such as silicon, silicon dioxide, silicon-on-insulator (SOI), strained silicon, gallium arsenide, coated substrates including those coated with silicon nitride, silicon oxynitride, titanium nitride, tantalum nitride, ultrathin gate oxides such as hafnium oxide, metal or metal coated substrates including those coated with titanium, tantalum, copper, aluminum, tungsten, alloys thereof, and combinations thereof. The surfaces of substrates herein can include critical dimension layers to be patterned including, for example, one or more gate-level layers or other critical dimension layer on the substrates for semiconductor manufacture. The substrates can be formed as circular wafers having dimensions such as, for example, 200 millimeters, 300 millimeters, or larger in diameter, or other dimensions useful for wafer fabrication.

The invention is further illustrated by the following examples.

Example 1

Synthesis of PAG-A1

Photoacid generator PAG-A1 was prepared by the multi-step synthesis illustrated in Scheme 2 and described the following paragraphs.

Scheme 2: Synthesis of PAG-A1

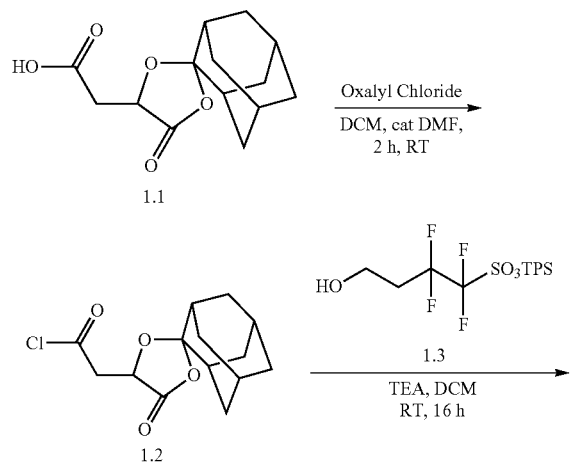

-continued

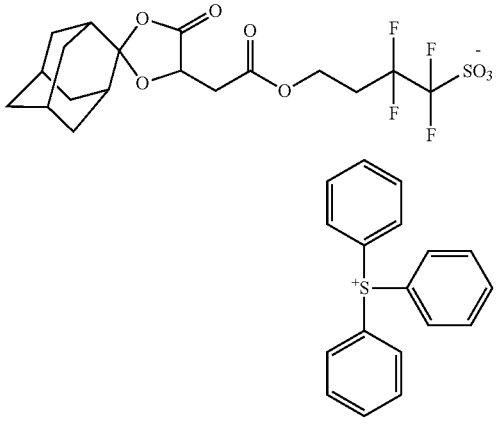

PAG-A1

2-(2,2-adamantyl-5-oxo-1,3-dioxolan-4-yl)acetyl chloride

To a solution of 2-(2,2-adamantyl-5-oxo-1,3-dioxolan-4-yl)acetic acid (1.1, 50 grams, 0.19 millimoles) in dichloromethane (350 milliliters) was added 1 mL of N,N-dimethylformamide Oxalyl chloride (35 milliliters, 0.38 mole) was added drop-wise and the resulting reaction mixture was stirred at room temp for 2 hours. Upon completion of the reaction, solvent was evaporated under reduced pressure to afford a white solid as product (1.2) which was used without any further purification. $^1$H NMR ((CD$_3$)$_2$CO, 300 MHz): δ 1.76 (m, 6H), 1.99 (m, 8H), 3.65 (m, 2H), 4.88 (t, 1H).

PAG-A1.

To a mixture of triphenylsulfonium 4-hydroxy-1,1,2,2-tetrafluorobutanesulfonate (1.3, 12 grams, 0.024 mole) and pyridine (3.94 grams, 0.05 mole) in acetonitrile (300 milliliters) at room temperature was added slowly a solution of 2-(2,2-adamantyl-5-oxo-1,3-dioxolan-4-yl)acetyl chloride (1.2, 7.5 grams, 0.025 mole) in acetonitrile (30 milliliters). The mixture was stirred at room temperature for 24 hours. Upon completion of reaction, solvent was evaporated, the residue was redissolved in dichloromethane (300 milliliters), washed with deionized water (300 milliliters) five times. The combined filtrate was evaporated to yield a crude product which was redissolved in dichloromethane (120 milliliters) and poured slowly through a syringe filter into 2 liters rapidly stirred methyl tert-butyl ether (MTBE). The gummy residue was dried under vacuum to yield PAG-A1 as an off-white solid (14 grams, 76% yield). $^1$H NMR (CDCl$_3$, 300 MHz): δ 1.70 (m, 9H), 2.01 (m, 5H), 2.79 (m, 4H), 4.42 (m, 2H), 4.74 (m, 1H), 7.73 (m, 15H). $^{19}$F NMR: δ—118.54, −112.59.

Example 2

Synthesis of PAG-A2

Photoacid generator PAG-A2 was prepared by a multi-step synthesis as illustrated in Scheme 3 and described in the following paragraph.

Scheme 3: Synthesis of PAG-A2

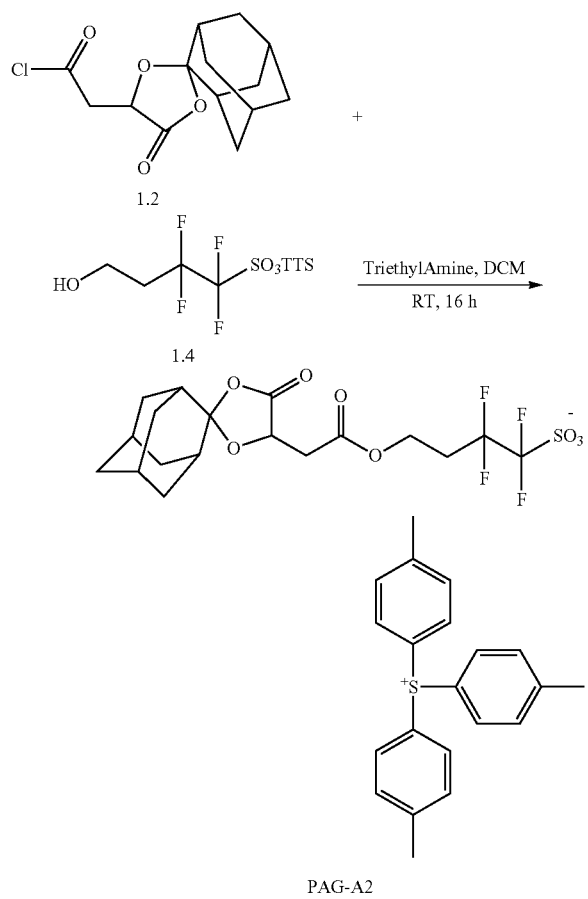

PAG-A2.

To a mixture of triphenylsulfonium 4-hydroxy-1,1,2,2-tetrafluorobutanesulfonate (1.4, 12.7 grams, 0.024 mole) and pyridine (3.94 grams, 0.05 mole) in acetonitrile (300 milliliters) at room temp was added slowly solution of 2-(2,2-adamantyl-5-oxo-1,3-dioxolan-4-yl)acetyl chloride (1.2, 7.5 grams, 0.025 mole) in acetonitrile (30 milliliters). The mixture was stirred at room temperature for 24 hours. Upon completion of reaction, solvent was evaporated, the residue was redissolved in dichloromethane (300 milliliters), and washed with deionized water (300 milliliters) five times. The combined filtrate was evaporated to yield crude product which was redissolved in dichloromethane (120 milliliters) and poured slowly through syringe filter into 2 liters rapidly stirred methyl tert-butyl ether (MTBE). The gummy residue was dried under vacuum to yield PAG-A2 as an off-white solid (13 grams, 67% yield). $^1$H NMR (CDCl$_3$, 300 MHz): δ 1.75 (m, 8H), 1.99 (m, 6H), 2.45 (s, 9H), 2.76 (m, 4H), 4.40 (m, 2H), 4.72 (m, 1H), 7.47 (d, 6H), 7.53 (d, 6H). $^{19}$F NMR: δ—118.65, −112.64.

Example 3

Synthesis of PAG-A3

Photoacid generator PAG-A3 was prepared by the multistep synthesis illustrated in Scheme 4 and described in the following paragraph.

Scheme 4: Synthesis of PAG-A3

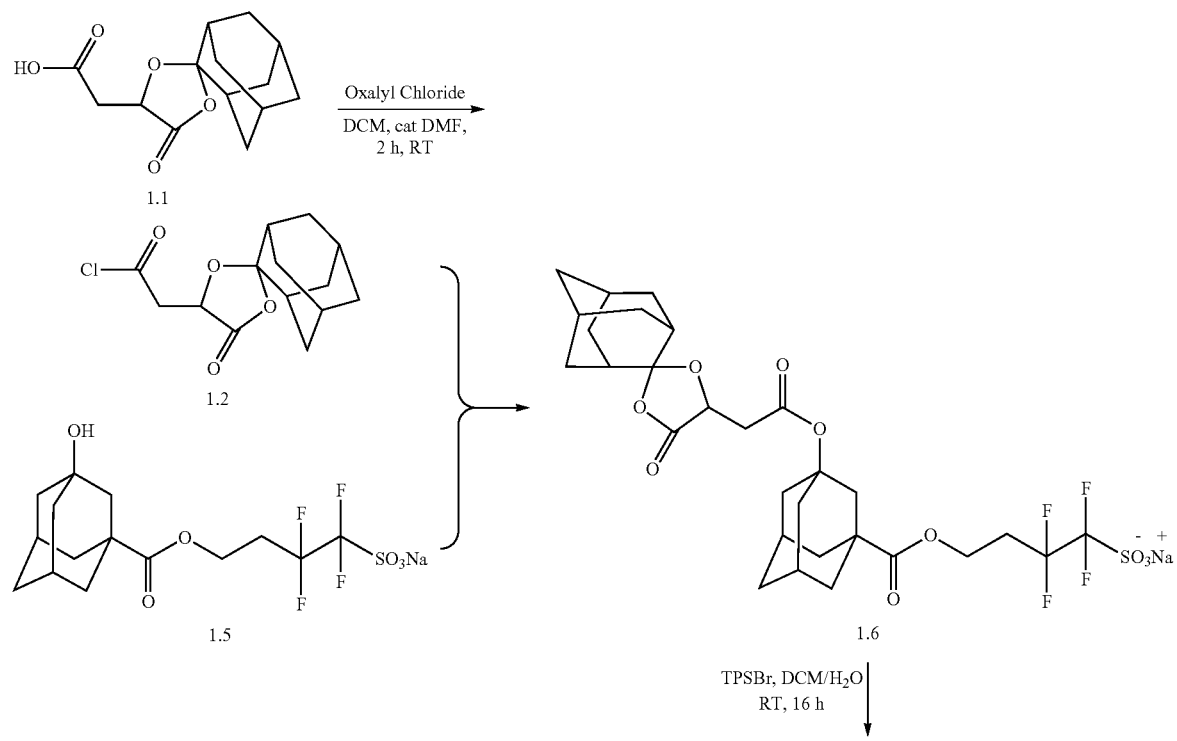

-continued

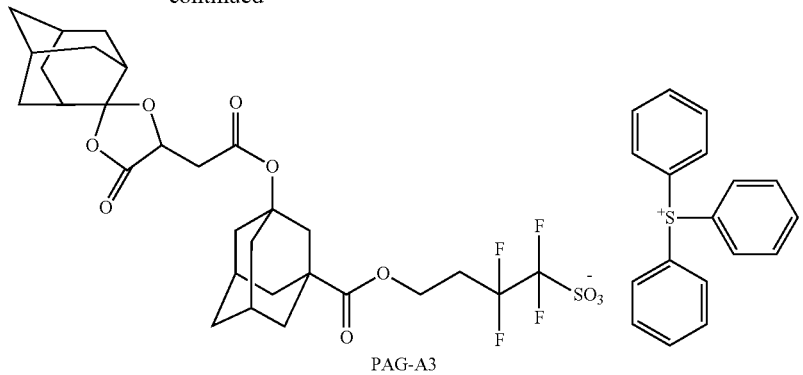

PAG-A3

Synthesis of PAG-A3:

To a mixture of compound 1.5 (20 grams, 0.046 mole; purchased from Heraeus DayChem) and triethylamine (9.26 grams, 0.12 mole) in acetonitrile (300 milliliters) at room temp was added slowly solution of 2-(2,2-adamantyl-5-oxo-1,3-dioxolan-4-yl)acetyl chloride: (1.2, 20 grams, 0.07 mole) in acetonitrile (30 mL). The mixture was heated to 50° C. for 24 hours. Upon completion of reaction, solvent was evaporated, the residue was redissolved in dichloromethane (300 milliliters), washed with deionized water (300 milliliters) five times. The combined filtrate was evaporated to yield crude product (1.6) which was redissolved in dichloromethane (500 milliliters) and water (500 milliliters). To this solution was added triphenylsulfonium bromide (5.1 grams, 0.015 mole) and stirred for 24 hours at room temperature. The organic phase was separated and washed with deionized water (300 milliliters) five times. The combined filtrate was evaporated to yield crude product which was redissolved in dichloromethane (120 mL) and poured slowly through a syringe filter into 2 liters rapidly stirred methyl tert-butyl ether (MTBE). The gummy residue was dried under vacuum to yield PAG-A3 as an off-white solid.

Example 5

Acid Diffusion Measurement

Acid diffusion measurements were determined by the following procedure. An acid detector layer formulation was prepared by combining an acid-cleavable polymer A1 (2-adamantyl-2-propyl methacrylate/alpha-(gamma-butyrolactone) methacrylate/1-hydroxyadamantyl-3-methacrylate terpolymer, 30/50/20 molar ratio, $M_w$=10,000 atomic mass units), shown below (5.981 weight percent of the total formulation):

polymer A1

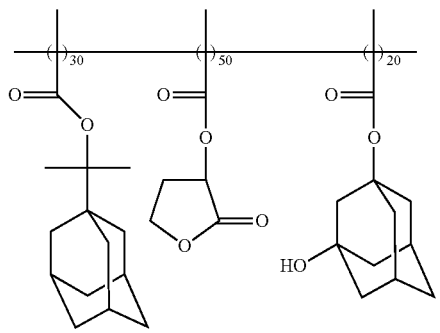

and tert-butyl 4-hydroxypiperidine-1-carboxylate as a quencher (0.019 weight percent of the total formulation) in a 50/50 (weight/weight) mixture of propylene glycol methyl ether acetate (PGMEA) and methyl 2-hydroxyisobutyrate (HBM). Separately, an acid source layer formulation was prepared by combining a t-butyl acrylate/methacrylic acid (70/30 mole percent, for 100 mole percent of monomers) copolymer (0.891 weight percent of formulation) and the PAG (153.40 micromoles/gram based on the total formulation) in an 80/20 (weight/weight) mixture of 2-methyl-1-butanol and decane. The acid detector layer formulation and acid source layer solutions were each filtered separately using a 0.2 micrometer polytetrafluoroethylene (PTFE) syringe filter.

The substrate (Si wafer, 200 millimeter diameter) was coated with AR™ 77 antireflective coating (available from Dow Electronic Materials) and baked at 205° C. for 60 seconds to form an antireflective layer of 84 nanometer thickness, and a 120 nanometer thickness of the acid detector layer formulation was coated on the antireflective layer with baking at 110° C. for 60 seconds. The acid source layer formulation was then coated on the acid detector layer and baked at 90° C. for 60 seconds. All coating processes were carried out on a TEL ACT 8 coating track manufactured by Tokyo Electron.

The coated wafer was then open-frame exposed over 100 dose increments (separate doses) starting from an initial dose of 1 millijoule/centimeter$^2$ at increments of 0.2 millijoule/centimeter$^2$ using a 193 nanometer exposure tool (ASML-1100, manufactured by ASML) and annular illumination. The wafer was post-exposure baked (PEB) at 110, 120, or 130° C. for 60 seconds. During the PEB step the acid released during exposure in the acid source layer diffused into the acid detector layer, causing deprotection of the acid labile group of the polymer of the acid detector layer. After PEB, the pattern was developed using 0.26 N aqueous tetramethylammonium hydroxide (TMAH) solution. The film thickness difference between the unexposed regions and exposed regions of the pattern is the total film loss ($\Delta L$). The greater the film thickness loss in the exposed region, the greater the acid diffusion.

The diffusivity of the PAG, D, is defined by Fick's law of diffusion (equation 1):

$$D=(\Delta L/2 * erfcE_{th}/E)2/t_{PEB} \qquad \text{(equation 1)}$$

where $\Delta L$ is the difference in thickness between the exposed and unexposed areas (also referred to herein as the film thickness loss), $t_{PEB}$ is the PEB time, erfc is the error function complement, $E_{th}$ is the exposure dose (in millijoules/centimeter$^2$) at which film thickness loss was observed for the first time, and E is the exposure dose (in millijoules/centimeter$^2$). Once the diffusivity was determined, the diffusion length, DL, was then calculated using equation 2:

$$DL=2*(D*t_{PEB})^{1/2} \qquad \text{(equation 2)}.$$

The diffusion length data for the exemplary and comparative PAGS are summarized in Table 1, below.

TABLE 1

Results of PAGs acid diffusion length

| Example | PAG cation | PAG anion | PAG acid diffusion length (nm) | | |
|---|---|---|---|---|---|
| | | | PEB = 110° C./60 sec | PEB = 120° C./60 sec | PEB = 130° C./60 sec |
| Compar. PAG 1 | triphenyl-sulfonium | | 42.1 | 87.1 | 118.4 |
| Compar. PAG 2 | triphenyl-sulfonium | | 21.2 | 55.9 | — |
| PAG-A2 | tri-p-tolyl-sulfonium | | 9.8 | 29.1 | 41.9 |

As can be seen in Table 1, the acid diffusion measurements indicate a shorter acid diffusion length for PAG-A2 at PEB temperatures of 110, 120 and 130° C. when compared with the comparative PAG 1 (TPSPFBuS) and PAG 2 (TPS Ad TFBS). These results demonstrate the utility of PAGs from the present invention on the manufacturing of highly resolving photoresists with excellent patterning characteristics.

Example 6

Lithographic Evaluation

The photoacid generators were evaluated lithographically according to the following procedure. Photoresists were formulated using the components and proportions shown in Table 2. The photoresist Polymer A2 was used in all examples. Polymer A2 is a pentapolymer incorporating monomers M1, M2, M3, M4 and M5, shown below.

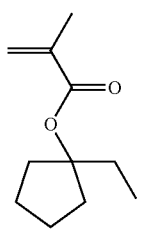

M1

-continued

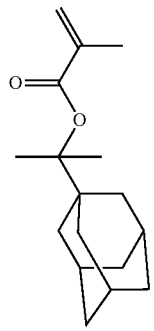

M2

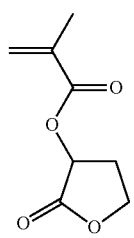

M3

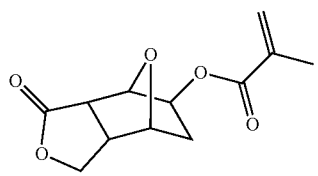

M4

-continued

M5

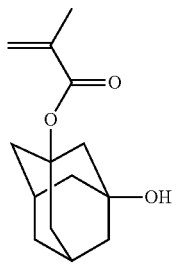

The mole percentage of M1/M2/M3/M4/M5 is 20/20/30/20/10 for a total of 100 mole percent of monomers. The weight average molecular weight ($M_w$) of the polymer was 8,000 atomic mass units. Note that the contents of PAG (see Table 2), base (t-butyloxycarbonyl-4-hydroxypyridine, TBOC-4HP), and surface leveling agent (surfactant) PF 656, available from Omnova, are in weight percent (wt %) based on 100% solids content, with the balance of the solids being the polymer. The solvents used in these formulations are PGMEA (S1) and HBM (S2). The final percent solids in both examples was 4 weight percent. The weight ratio of solvent S1:S2 in the final formulation was 1:1. Structures of Comparative PAG 1, Comparative PAG 2, and Inventive PAG-A1 are shown in Table 2.

Photoresist formulation compositions for Comparative Examples 1, 2 and Example 1 are shown in Table 3 below:

TABLE 3

| Sample | PAG | PAG (wt %) | Base (wt %) | SLA (wt %) |
|---|---|---|---|---|
| Comparative Example 1 | Comparative PAG 1 | 11.36 | 1.03 | 0.1 |
| Comparative Example 2 | Comparative PAG 2 | 9.59 | 1.03 | 0.1 |
| Example 1 | PAG-A1 | 12.56 | 1.03 | 0.1 |

The above photoresists were lithographically processed as follows. The photoresist was spin coated onto a 200 millimeter diameter silicon wafer having an 84 nanometer thick organic antireflective coating (AR™ 77, Dow Electronic Materials) and baked at 110° C. for 60 seconds to form a resist film 100 nanometers thick. The photoresist was exposed with ArF excimer laser (193 nanometers) through a mask pattern targeting a line and space pattern (L/S pattern) having a line width of 90 nanometers and a pitch of 180 nanometers, using an ArF exposure apparatus ASML-1100 (manufactured by ASML), NA (numerical aperture)=0.75 under annular illumination with outer/inner sigma of 0.89/0.64 with focus offset/step 0.10/0.05. The wafers were post-exposure baked at 100°

TABLE 2

| PAG | PAG Name | Structure of the PAG |
|---|---|---|
| Comparative PAG 1 | TPS AdOH TFBS | |
| Comparative PAG 2 | Triphenylsulfonium perfluorobutanesulfonate | |
| Inventive PAG-A1 | TPS AdDOT TFBS | |

C. for 60 seconds followed by developing with 0.26 N aqueous tetramethylammonium hydroxide (TMAH) developer and subsequent water wash.

In each example, a line/space (L/S) pattern having a line width of 90 nanometers and a pitch of 180 nanometers was formed. Mask Error Factor (MEF) and Exposure Latitude (EL) were determined by processing the image captured by top-down scanning electron microscopy (SEM) using a Hitachi 9380 CD-SEM, operating at an accelerating voltage of 800 volts (V), probe current of 8.0 picoamperes (pA), using 200 Kx magnification. Exposure latitude (EL) was defined as a difference in exposure energy to print +/−10% of the target diameter normalized by the sizing energy. Mask Error Factor (MEF) was defined as the ratio of critical dimension (CD) change on the resolved resist pattern to the dimension change on the mask pattern.

The results from the lithographic evaluation of the above photoresist formulations using AR™ 77 as substrate are reported in Table 4.

TABLE 4

| PAG | Eo | EL % | MEF | LWR |
|---|---|---|---|---|
| Comparative PAG 1 | 7.1 | 13.04 | 3.42 | 13.6 |
| Comparative PAG 2 | 5.3 | 7.02 | 4.17 | 12.6 |
| PAG-A1 | 11.4 | 14.46 | 3.33 | 12.6 |

As seen in Table 4, the Example 1 photoresist comprising inventive PAG-A1 exhibited improved lithographic performance in terms of exposure latitude, and Mask Error Factor and Line width roughness (LWR).

The above photoresists were also lithographically processed after coating on a different substrate. The photoresist was spin coated onto a 200 millimeter silicon wafer having an 84 nanometer thick Silicon antireflective coating (XS080532AA/XS110532AA/HMDS, SiARC, Dow Electronic Materials) and baked at 110° C. for 60 seconds, to form a resist film 100 nanometers thick. The photoresist was exposed with ArF excimer laser (193 nm) through a mask pattern targeting a line and space (L/S) pattern having a line width of 80 nanometers and a pitch of 160 nanometers, using an ArF exposure apparatus ASML-1100 (manufactured by ASML), NA (numerical aperture)=0.75 under annular illumination with outer/inner sigma of 0.89/0.64 with focus offset/step 0.10/0.05. The wafers were post-exposure baked at 100° C. for 60 seconds followed by developing with 0.26 N aqueous tetramethylammonium hydroxide (TMAH) developer and subsequent water wash.

The results from the lithographic evaluation of the above photoresist formulations using SiARC as substrate are reported in Table 5.

TABLE 5

| PAG | Eo | EL % | MEF | LWR |
|---|---|---|---|---|
| Comparative PAG 2 | 4.6 | 16.09 | 2.60 | 6.8 |
| PAG-A1 | 8.6 | 22.32 | 1.84 | 6.2 |

As seen in Table 5, photoresist that comprise PAG-A1 exhibit improved lithographic performance in terms of exposure latitude, and Mask Error Factor and Line width roughness (LWR).

The invention claimed is:

1. A photoacid generator compound having the formula (1)

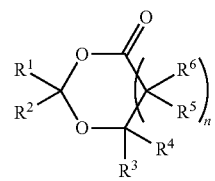

wherein
n is zero or 1; and
$R^1$ and $R^2$ are each independently halogen, unsubstituted or substituted $C_{1-20}$ linear or branched alkyl, unsubstituted or substituted $C_{1-20}$ cycloalkyl, unsubstituted or substituted $C_{6-20}$ aryl, unsubstituted or substituted $C_{3-20}$ heteroaryl, or a monovalent group having the structure

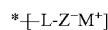

wherein L is an unsubstituted or substituted $C_{1-50}$ divalent group; $Z^-$ is a monovalent anionic group selected from carboxylate, sulfate, sulfonate, sulfamate, sulfonamidate, and sulfonimidate; and $M^+$ is a cation selected from disubstituted iodonium ions and trisubstituted sulfonium ions; wherein R' and $R^2$ can be taken together to form a ring;
$R^3$, $R^4$, $R^5$, and $R^6$ are each independently hydrogen, halogen, unsubstituted or substituted $C_{1-20}$ linear or branched alkyl, unsubstituted or substituted $C_{1-20}$ cycloalkyl, unsubstituted or substituted $C_{6-20}$ aryl, unsubstituted or substituted $C_{3-20}$ heteroaryl, or a monovalent group having the structure

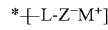

wherein L is an unsubstituted or substituted $C_{1-50}$ divalent group; $Z^-$ is a monovalent anionic group selected from carboxylate, sulfate, sulfonate, sulfamate, sulfonamidate, and sulfonimidate; and $M^+$ is a cation selected from disubstituted iodonium ions and trisubstituted sulfonium ions; wherein
$R^3$ and $R^4$ can be taken together to form a ring and/or
$R^5$ and $R^6$ can be taken together to form a ring,
provided that no more than two rings are collectively formed by $R^1$, $R^2$, $R^3$, $R^4$, $R^5$, and $R^6$, and
provided that one of R', $R^2$, $R^3$, $R^4$, $R^5$, and $R^6$ has the structure

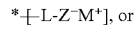, or $R^1$ and $R^2$ are taken together to form

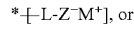, or $R^3$ and $R^4$ are taken together to form

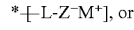, or $R^5$ and $R^6$ are taken together to form

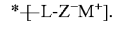.

2. The photoacid generator compound of claim 1, having the formula (2a)

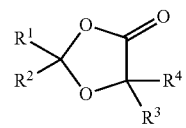

wherein
R³ or R⁴ is

*—[L-SO₃⁻M⁺], or

R³ and R⁴ are taken together to form

*=[L-SO₃⁻M⁺]; and

R¹, R², L, and M⁺ are as defined in claim 1.

3. The photoacid generator compound of claim 2, wherein L is a substituted $C_{1-50}$ divalent group, L', having the formula (3)

$$*-[(Y)_m-W^1-X-\underset{R^8}{\overset{R^7}{C}}]-*  \quad (3)$$

wherein
m is zero or 1,
Y is an unsubstituted or substituted $C_{1-20}$ alkylene,
$W^1$ is an unsubstituted or substituted divalent $C_{5-20}$ alicyclic group,
X is an unsubstituted or substituted $C_{1-20}$ alkylene, and
$R^7$ and $R^8$ are each independently fluorine, or partially fluorinated $C_{1-12}$ alkyl, or perfluorinated $C_{1-12}$ alkyl.

4. The photoacid generator compound of claim 3, wherein m is 1.

5. The photoacid generator compound of claim 1, having the formula (2b)

(2b)

wherein
R¹ or R² is

*—[L-SO₃⁻M⁺], or

R¹ and R² are taken together to form

*=[L-SO₃⁻M⁺]; and

R³, R⁴, L, and M⁺ are as defined in claim 1.

6. The photoacid generator compound of claim 1, comprising

31
-continued

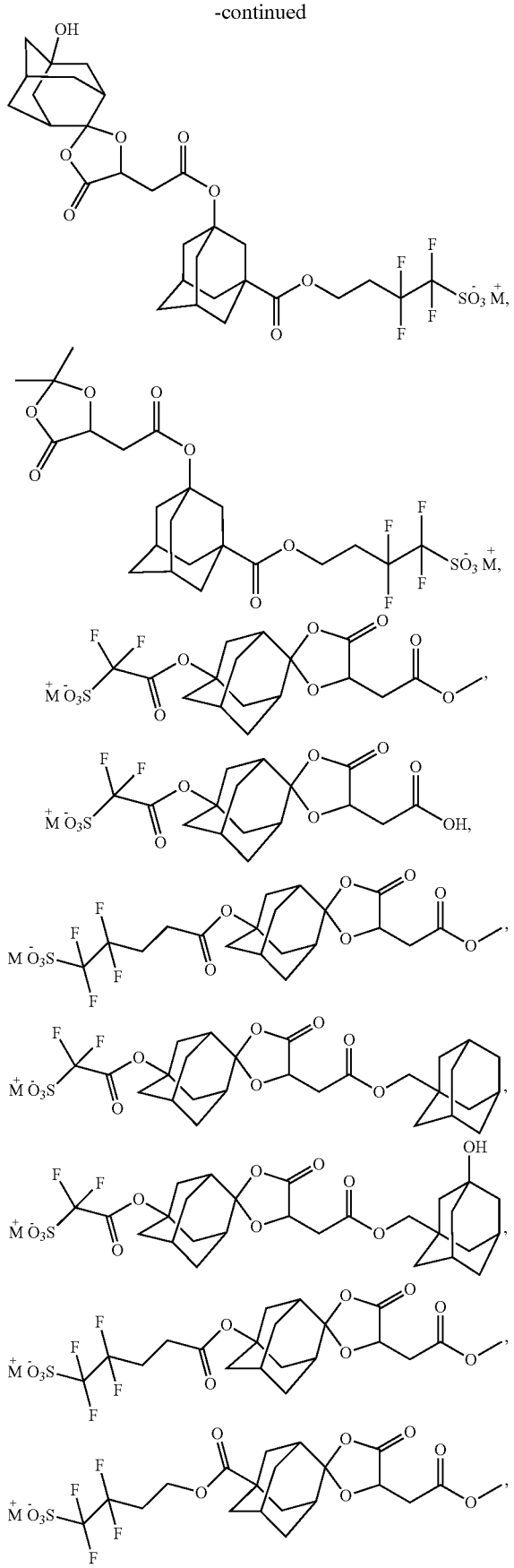

32
-continued

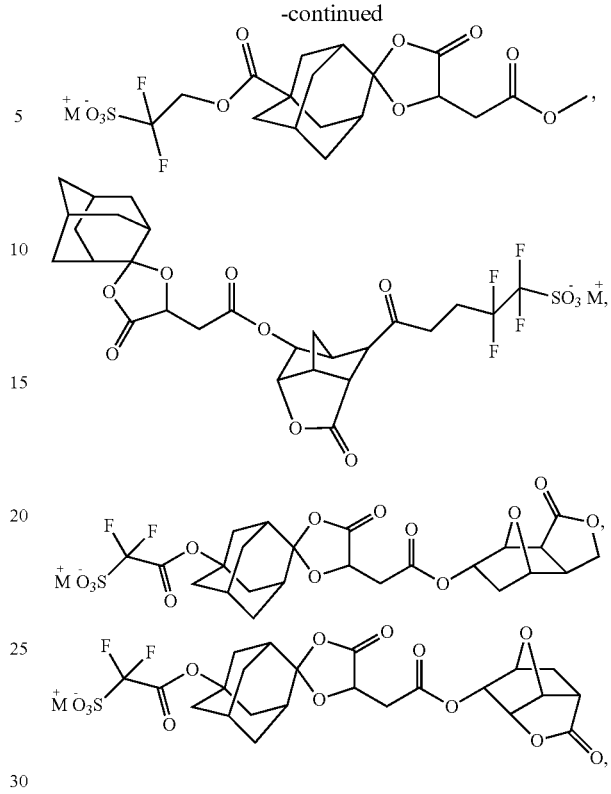

or a combination thereof; wherein M⁺ is as defined in claim 1.

7. A photoresist composition comprising:
an acid-sensitive polymer, and
the photoacid generator compound of claim 1.

8. A coated substrate comprising:
(a) a substrate having one or more layers to be patterned on a surface thereof; and
(b) a layer of the photoresist composition of claim 7 over the one or more layers to be patterned.

9. A method of forming an electronic device, comprising:
(a) applying a layer of a photoresist composition of claim 7 on a substrate;
(b) pattern-wise exposing the photoresist composition layer to activating radiation; and
(c) developing the exposed photoresist composition layer to provide a resist relief image.

10. The method of claim 9, wherein the activating radiation is extreme ultraviolet (EUV) or electron-beam radiation.

11. The method of claim 9, wherein the photoacid generator compound has the formula (2a)

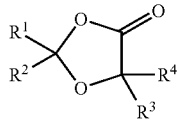

(2a)

wherein
$R^3$ or $R^4$ is

*—[—L—SO$_3^-$M⁺], or $R^3$ and $R^4$ are taken together to form

*—[—L—SO$_3^-$M⁺]; and $R^1$, $R^2$, L, and M⁺ are as defined in claim 1.

12. The method of claim 11, wherein L is a substituted $C_{1-50}$ divalent group, $L_1$, having the formula (3)

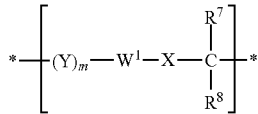
(3)

wherein m is zero or 1,

Y is an unsubstituted or substituted $C_{1-20}$ alkylene, $W^1$ is an unsubstituted or substituted divalent $C_{5-20}$ alicyclic group, X is an unsubstituted or substituted $C_{1-20}$ alkylene, and $R^7$ and $R^8$ are each independently fluorine, or partially fluorinated $C_{1-12}$ alkyl, or perfluorinated $C_{1-12}$ alkyl.

13. The method of claim 12, wherein m is 1.

14. The method of claim 9, wherein the photoacid generator compound has the formula (2b)

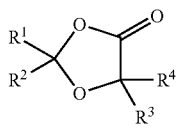
(2b)

wherein $R^1$ or $R^2$ is

*—[—L-SO$_3^-$M$^+$], or $R^1$ and $R^2$ are taken together to form

*—[—L-SO$_3^-$M$^+$]; and $R^3$, $R^4$, L, and M$^+$ are as defined in claim 1.

15. The photoresist composition of claim 7, wherein the photoacid generator compound has the formula (2a)

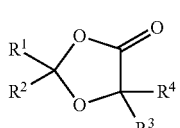
(2a)

wherein $R^3$ or $R^4$ is

*—[—L-SO$_3^-$M$^+$], or $R^3$ and $R^4$ are taken together to form

*—[—L-SO$_3^-$M$^+$]; and $R^1$, $R^2$, L, and M$^+$ are as defined in claim 1.

16. The photoresist composition of claim 15, wherein L is a substituted $C_{1-50}$ divalent group, $L^1$, having the formula (3)

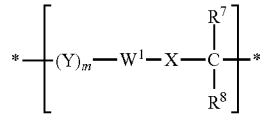
(3)

wherein m is zero or 1,

Y is an unsubstituted or substituted $C_{1-20}$ alkylene, $W^1$ is an unsubstituted or substituted divalent $C_{5-20}$ alicyclic group, X is an unsubstituted or substituted $C_{1-20}$ alkylene, and $R^7$ and $R^8$ are each independently fluorine, or partially fluorinated $C_{1-12}$ alkyl, or perfluorinated $C_{1-12}$ alkyl.

17. The photoresist composition of claim 16, wherein m is 1.

18. The photoresist composition of claim 7, wherein the photoacid generator compound has the formula (2b)

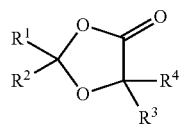
(2b)

wherein $R^1$ or $R^2$ is

*—[—L-SO$_3^-$M$^+$], or $R^1$ and $R^2$ are taken together to form

*—[—L-SO$_3^-$M$^+$]; and $R^3$, $R^4$, L, and M$^+$ are as defined in claim 1.

19. A photoacid generator compound having the formula (2b)

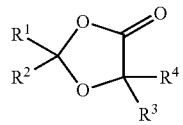
(2b)

wherein $R^1$ is

*—[—L-SO$_3^-$M$^+$], wherein L is a substituted $C_{1-50}$ divalent group, $L^2$, having the structure

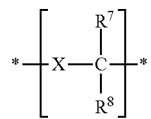

wherein X is an unsubstituted or substituted $C_{1-20}$ alkylene; $R^7$ and $R^8$ are each independently fluorine, or partially fluorinated $C_{1-12}$ alkyl, or perfluorinated $C_{1-12}$ alkyl; and M$^+$ is a cation selected from disubstituted iodonium ions and trisubstituted sulfonium ions;

$R^2$ and $R^3$ are hydrogen;
$R^4$ has the structure $$*-[(Y)_m-W^2]$$

wherein m is zero or 1, Y is an unsubstituted or substituted $C_{1-20}$ alkylene, and $W^2$ is an unsubstituted or substituted monovalent $C_{5-20}$ alicyclic group.

* * * * *